(12) United States Patent
Takayanagi et al.

(10) Patent No.: US 9,198,594 B2
(45) Date of Patent: Dec. 1, 2015

(54) TWA MEASURING APPARATUS AND TWA MEASURING METHOD

(71) Applicant: NIHON KOHDEN CORPORATION, Shinjuku-ku, Tokyo (JP)

(72) Inventors: Tsuneo Takayanagi, Tokyo (JP); Takashi Kaiami, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 33 days.

(21) Appl. No.: 14/149,968

(22) Filed: Jan. 8, 2014

(65) Prior Publication Data

US 2014/0194764 A1 Jul. 10, 2014

(30) Foreign Application Priority Data

Jan. 10, 2013 (JP) ................... 2013-002859

(51) Int. Cl.
*A61B 5/0452* (2006.01)
*A61B 5/0472* (2006.01)

(52) U.S. Cl.
CPC ............. *A61B 5/0452* (2013.01); *A61B 5/0472* (2013.01); *A61B 5/04525* (2013.01)

(58) Field of Classification Search
CPC . A61B 5/0452; A61B 5/04525; A61B 5/0472
See application file for complete search history.

(56) References Cited

U.S. PATENT DOCUMENTS

| 5,935,082 | A | 8/1999 | Albrecht et al. |
| 6,668,189 | B2 | 12/2003 | Kaiser et al. |
| 2003/0060724 | A1 | 3/2003 | Thiagarajan et al. |
| 2005/0004481 | A1 | 1/2005 | Xue et al. |
| 2005/0234363 | A1 | 10/2005 | Xue |

OTHER PUBLICATIONS

Search Report dated Apr. 16, 2014, issued by the European Patent Office in counterpart European Application No. 14150694.9.

*Primary Examiner* — Joseph Dietrich
(74) *Attorney, Agent, or Firm* — Sughrue Mion, PLLC

(57) ABSTRACT

A TWA measuring apparatus includes: a T-wave feature quantity measuring section; a classifying section classifying T-wave feature quantities into groups of odd and even electrocardiogram waveforms; a reliability index calculating section calculating: first and second representative values and first and second dispersion values of the T-wave feature quantities in the odd and even group; a difference between the first and second representative values, to obtain a TWA feature quantity; and an adjustment value between the first representative value and the first dispersion value, and an adjustment value between the second representative value and the second dispersion value, to obtain a reliability index; and a reliability recognizing section recognizing: when the reliability index exceeds a threshold, that reliability of the TWA feature quantity is high; and when the reliability index does not exceed the threshold, that the reliability is low.

13 Claims, 8 Drawing Sheets

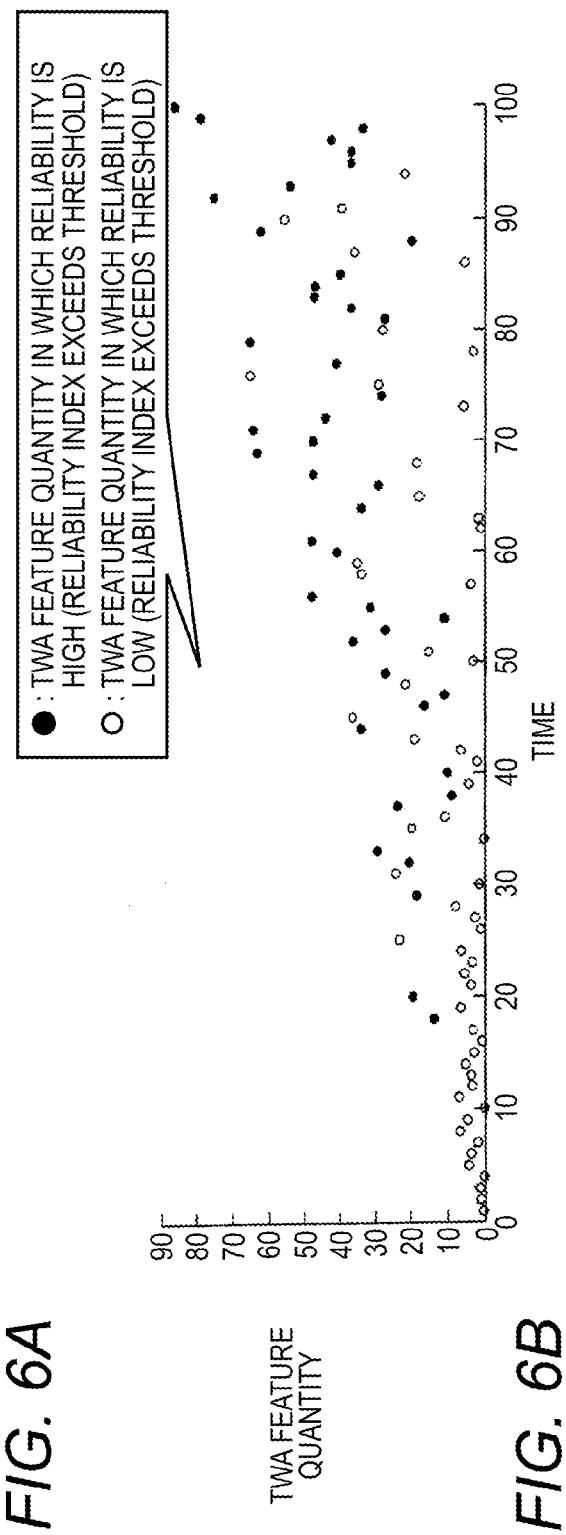
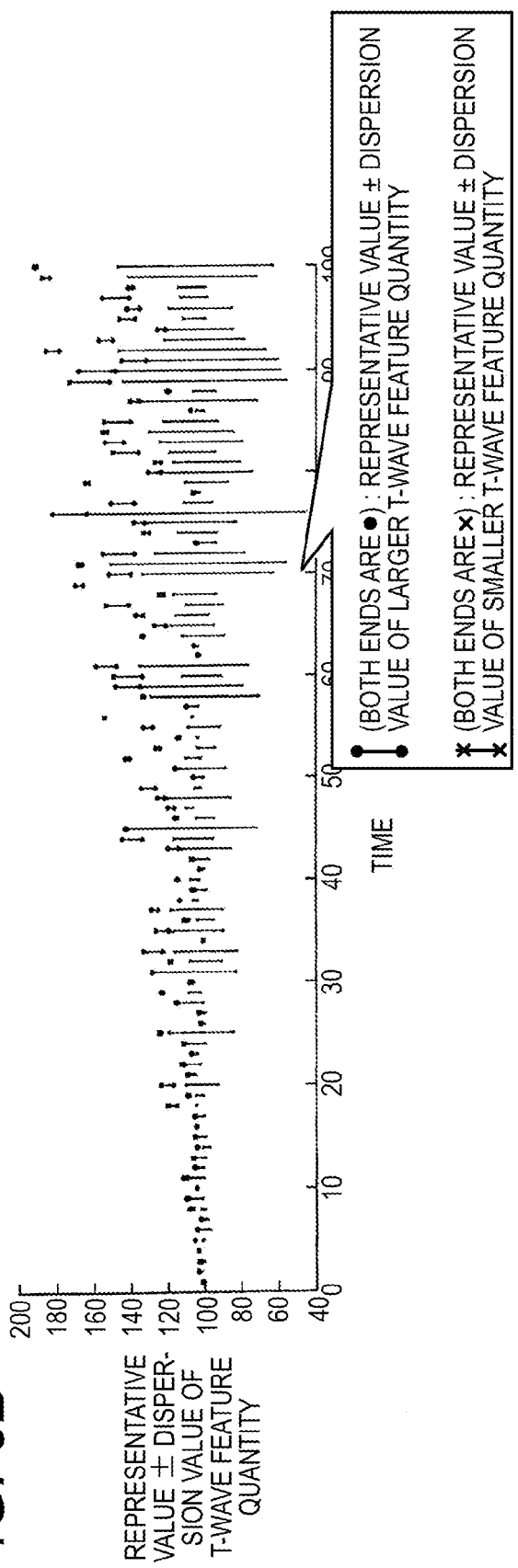
FIG. 6A
FIG. 6B

TWA MEASURING APPARATUS AND TWA MEASURING METHOD

CROSS-REFERENCE TO RELATED APPLICATION(S)

This application is based upon and claims the benefit of priority from prior Japanese patent application No. 2013-002859, filed on Jan. 10, 2013, the entire contents of which are incorporated herein by reference.

BACKGROUND

The presently disclosed subject matter relates to a TWA measuring apparatus and TWA measuring method which can accurately measure TWA (T-wave alternans).

TWA appears at onset of illness such as QT prolongation syndrome, variant angina, acute myocardial ischemia, electrolyte abnormality, paroxysmal tachycardia, bradycardia, or pericardial fluid accumulation. TWA is a phenomenon in which the amplitude and polarity of the T wave appearing in an electrocardiogram are alternately changed, and an index effective to predict sudden cardiac death. TWA is not a phenomenon which can be always observed with the naked eye, and therefore its application in clinics is limited.

From the 1980s, consequently, techniques for enabling a microvolt level of TWA (Microvolt TWA: MTWA) to be measured by a computer have been developed.

Examples of currently proposed techniques for measuring TWA are a measurement technique based on the MMA (Modified Moving Average) method of General Electric (GE) Company, and that based on the periodogram of Cambridge Heart (CH), Inc. which are disclosed in U.S. Pat. No. 6,668,189 and U.S. Pat. No. 5,935,082, respectively.

In the measurement technique of GE Company, TWA is measured from the amplitude difference of T-waves between the average waveform of odd-numbered beats (hereinafter, referred to as odd beats) and that of even-numbered beats (hereinafter, referred to as even beats). The measurement technique of GE Company is directed to a method of analyzing a waveform in a time domain, and is said to have resistance to noises. However, the technique does not have a long history as a measurement technique, and it is required to watch its clinical effect.

In the measurement technique of CH Inc., by contrast, TWA is measured by performing a spectrum analysis of an electrocardiogram derived from special electrodes. The measurement technique of CH Inc. has been used from the 1980s, and hence its effectiveness in clinics has been proved.

Today, therefore, it is considered that the measurement technique based on the periodogram of CH Inc. is clinically more useful than that based on the MMA method of GE Company.

With respect to the measurement technique based on the periodogram of CH Inc., after its announcement, various techniques for performing new processes, such as a technique of measurement electrodes are added, and still now the added latest techniques have been used.

TWA is a phenomenon in which T waves of odd and even beats are alternately changed. In the related-art technique for measuring TWA based on the periodogram disclosed in U.S. Pat. No. 5,935,082, a value (alternans voltage) indicative of the magnitude of TWA, and a value (alternans rate) indicative of the reliability of the value indicating the magnitude of TWA are calculated, and, when the magnitudes of the values are equal to or larger than predetermined values, respectively, it is determined that TWA exists.

In the related art, as described above, the presence/absence of TWA can be determined, but the states of odd and even beats cannot be sufficiently known. Moreover, it is impossible also to objectively know the reliability of the value indicating the magnitude of TWA.

SUMMARY

The presently disclosed subject matter may provide a TWA measuring apparatus and TWA measuring method in which the states of odd and even beats can be known, and also the reliability of the value indicating the magnitude of TWA (hereinafter, such a value is referred to as the TWA feature quantity) can be known.

The TWA measuring apparatus may comprise: a T-wave feature quantity measuring section which is configured to measure T-wave feature quantities of electrocardiogram waveforms acquired from a subject; a classifying section which is configured to classify the T-wave feature quantities into a group of odd electrocardiogram waveforms and a group of even electrocardiogram waveforms; a reliability index calculating section which is configured to calculate: a first representative value and a first dispersion value of the T-wave feature quantities in the group of odd electrocardiogram waveforms, and a second representative value and a second dispersion value of the T-wave feature quantities in the group of even electrocardiogram waveforms; a difference between the first and second representative values, to obtain a TWA feature quantity; and an adjustment value between the first representative value and the first dispersion value, and an adjustment value between the second representative value and the second dispersion value, to obtain a reliability index; and a reliability recognizing section which is configured to recognize: when the reliability index exceeds a threshold, that reliability of the TWA feature quantity is high; and when the reliability index does not exceed the threshold, that the reliability of the TWA feature quantity is low.

The reliability index calculating section may calculate: when the first representative value is larger than the second representative value, a difference between the first representative value and the first dispersion value, to obtain a first difference value, and a sum of the second representative value and the second dispersion value, to obtain a first sum value; and, when the first representative value is smaller than the second representative value, a difference between the second representative value and the second dispersion value, to obtain a first difference value, and a sum of the first representative value and the first dispersion value, to obtain a first sum value. The reliability index calculating section may calculate a difference between the first difference value and the first sum value, to obtain the reliability index.

The TWA measuring apparatus may further comprise: a displaying section which is configured to display the TWA feature quantity and the reliability index.

The TWA measuring method may comprise: measuring T-wave feature quantities of electrocardiogram waveforms acquired from a subject; classifying the T-wave feature quantities into a group of odd electrocardiogram waveforms and a group of even electrocardiogram waveforms; calculating: a first representative value and a first dispersion value of the T-wave feature quantities in the group of odd electrocardiogram waveforms, and a second representative value and a second dispersion value of the T-wave feature quantities in the group of even electrocardiogram waveforms; a difference between the first and second representative values, to obtain a TWA feature quantity; and an adjustment value between the first representative value and the first dispersion value, and an adjustment value between the second representative value and the second dispersion value, to obtain a reliability index; and recognizing: when the reliability index exceeds a threshold, that the reliability of the TWA feature quantity is high; and, when the reliability index does not exceed the threshold, that the reliability of the TWA feature quantity is low.

In the calculating process, when the first representative value is larger than the second representative value, a difference between the first representative value and the first dispersion value is calculated, to obtain a first difference value, and a sum of the second representative value and the second dispersion value is calculated, to obtain a first sum value; and, when the first representative value is smaller than the second representative value, a difference between the second representative value and the second dispersion value is calculated, to obtain a first difference value, and a sum of the first representative value and the first dispersion value is calculated to obtain a first sum value. A difference between the first difference value and the first sum value may be calculated, to obtain the reliability index.

The TWA measuring method may further comprise: displaying the TWA feature quantity and the reliability index.

The measuring process may comprise: storing the electrocardiogram waveforms acquired from the subject; and measuring the T-wave feature quantities of the stored electrocardiogram waveforms.

The process of measuring the T-wave feature quantities of the stored electrocardiogram waveforms may comprise: determining whether, with respect to the stored electrocardiogram waveforms, a beat is a dominant beat or an ectopic beat; and, when a number of the dominant beats is not equal to or larger than a designated number, determining that the measurement is disabled, and, when the number of the dominant beats is equal to or larger than the designated number, extracting an electrocardiograph of a zone where only the dominant beats exist.

The first and second representative values and the first and second dispersion values of the T-wave feature quantities may be values which are obtained by statistically processing the T-wave feature quantities.

Each of the first and second representative values of the T-wave feature quantities may be an average or medium of the T-wave feature quantities, and each of the first and second dispersion values of the T-wave feature quantities may be a standard deviation or root mean square of the T-wave feature quantities.

Each of the T-wave feature quantities is one of a width, amplitude, area, and frequency of a T-wave of the corresponding one of the electrocardiogram waveforms, or a value which is obtained by performing a four arithmetic operation on an arbitrary combination of the width, amplitude, area, and frequency.

BRIEF DESCRIPTION OF THE DRAWINGS

FIG. 6A is a view illustrating TWA feature quantities, and FIG. 6B is a view illustrating representative value and dispersion value of and T-wave feature quantities (applied to Embodiments 1 and 2).

DETAILED DESCRIPTION OF EXEMPLARY EMBODIMENTS

The TWA measuring apparatus and TWA measuring method of the presently disclosed subject matter will be described in detail with respect to Embodiment 1 and Embodiment 2 with reference to the drawings.

When the TWA measuring apparatus and TWA measuring method of the presently disclosed subject matter are used, the states of odd and even beats can be known from an electrocardiographic signal which can be obtained by various methods, and the reliability of the TWA measurement can be ensured.

Specifically, the states of odd and even beats, and the reliability of the TWA feature quantity can be known from an electrocardiographic signal acquired by a measuring method such as a Frank's vector electrocardiogram, and a usual scalar electrocardiogram, i.e., a standard 12-lead electrocardiogram, a derived lead electrocardiogram, a Holter electrocardiogram, an event electrocardiogram, an exercise electrocardiogram, and a monitoring electrocardiogram.

In the specification, the term "patient" is used as a specific example of the subject. However, the patient means not only a patient who is examined in a hospital, but also a user of a facility other than a hospital, such as a detection center or clinic in which a physical examination is performed, or an ordinary house.

Embodiment 1

Figure 1:
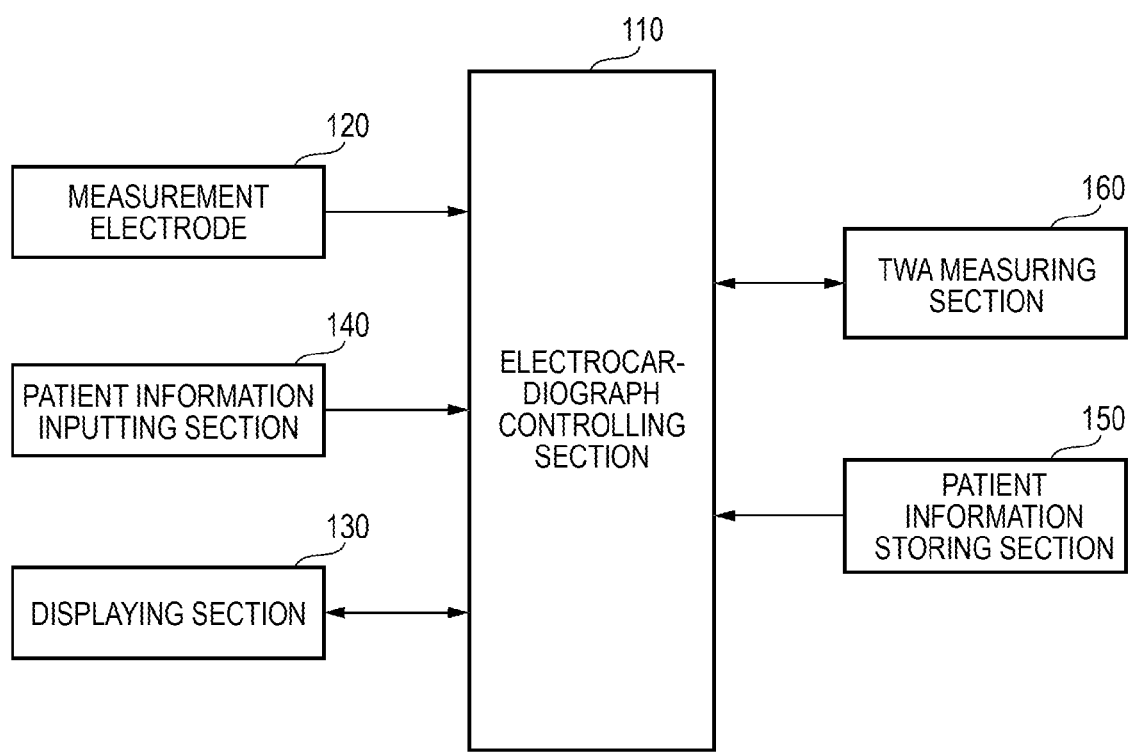
FIG. 1 is a block diagram of a TWA measuring apparatus of Embodiment 1.

Hereinafter, a TWA measuring apparatus and TWA measuring method of Embodiment 1 will be described. In the embodiment, the states of odd and even beats, and the reliability of the TWA feature quantity are known from electrocardiogram waveforms of odd and even beats which are obtained by measurement electrodes of an electrocardiograph. The embodiment may be applied also to a Holter electrocardiogram analyzer or a biological information monitor in place of an electrocardiograph, Configuration of TWA Measuring Apparatus FIG. 1 is a block diagram of the TWA measuring apparatus of Embodiment 1. The TWA measuring apparatus of Embodiment 1 is disposed in an electrocardiograph.

As shown in the figure, the TWA measuring apparatus 100 includes an electrocardiograph controlling section 110, measurement electrodes 120, a displaying section 130, a patient information inputting section 140, a patient information storing section 150, and a TWA measuring section 160.

The electrocardiograph controlling section 110 generally controls the operations of the measurement electrodes 120, the displaying section 130, the patient information inputting section 140, the patient information storing section 150, and the TWA measuring section 160.

The measurement electrodes 120 are electrodes which are to be attached to the body surface of the patient. The number and attachment positions of the used measurement electrodes 120 are different depending on the employed measuring method.

The displaying section 130 displays the electrocardiographic signal which is acquired by the measurement electrodes 120, patient information which is supplied from the patient information inputting section 140, other patient information which is stored in the patient information storing section 150, and a result of measurement of TWA such as the TWA feature quantity and a reliability index.

The patient information inputting section 140 is used for inputting patient information by means of key operations of the measuring person. The patient information contains a patient ID, the name of the patient, the age of the patient, and the sex of the patient.

The patient information storing section 150 stores the patient information which is input through the patient information inputting section 140, namely, the patient ID, the name of the patient, the age of the patient, and the sex of the patient.

The TWA measuring section 160 obtains the states of odd and even beats by using the electrocardiogram waveforms stored in the electrocardiograph controlling section 110, and calculates the TWA feature quantity and the reliability index.

Figure 2:
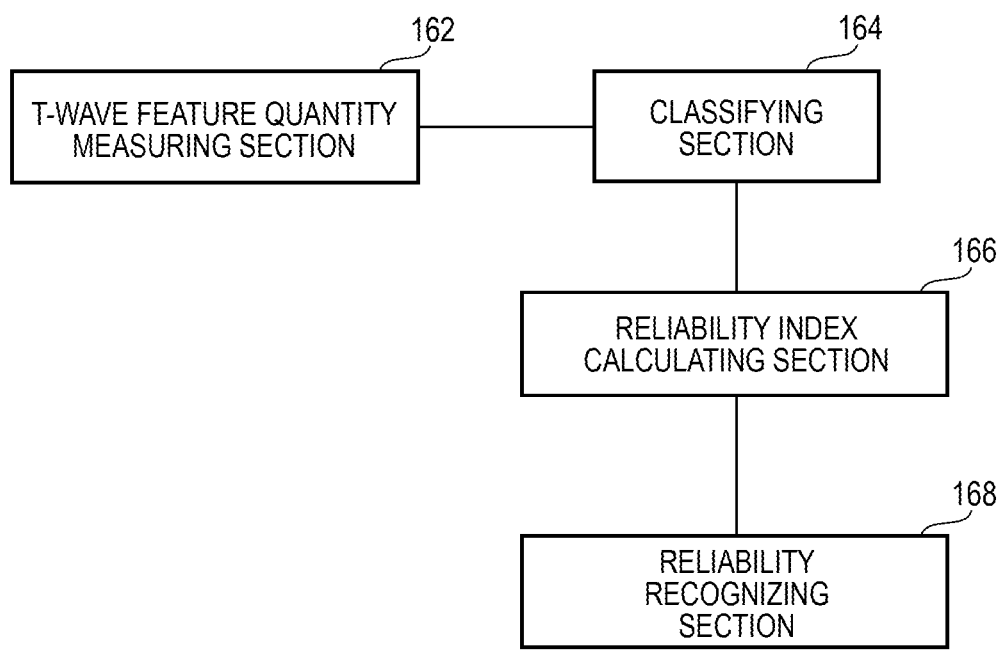
FIG. 2 is a block diagram of a TWA measuring section shown in FIG. 1.

FIG. 2 is a block diagram of the TWA measuring section 160 shown in FIG. 1. The TWA measuring section 160 includes a T-wave feature quantity measuring section 162, a classifying section 164, a reliability index calculating section 166, and a reliability recognizing section 168.

The T-wave feature quantity measuring section 162 measures a T-wave feature quantity of an electrocardiogram waveform acquired from the subject. The T-wave feature quantity is one of the width, amplitude, area, and frequency of a T-wave of the electrocardiogram waveform, or a value which is obtained by performing a four arithmetic operation on an arbitrary combination of these values.

The classifying section 164 classifies the T-wave feature quantities of the electrocardiogram waveforms into a group of odd electrocardiogram waveforms and a group of even electrocardiogram waveforms.

The reliability index calculating section 166 calculates a representative value and a dispersion value of the T-wave feature quantities in each of the groups, further calculates a difference of the representative values of the T-wave feature quantities of the groups to obtain the TWA feature quantity, and further calculates an adjustment value between the representative value and dispersion value of the T-wave feature quantities in the group of odd electrocardiogram waveforms, and an adjustment value between the representative value and dispersion value of the T-wave feature quantities in the group of even electrocardiogram waveforms, to obtain the reliability index.

More specifically, the reliability index calculating section 166 calculates the difference between the representative values of the T-wave feature quantities of the groups to obtain the TWA feature quantity, further calculates a difference between a larger one of the representative value of the T-wave feature quantities in the group of odd electrocardiogram waveforms and the representative value of the T-wave feature quantities in the group of even electrocardiogram waveforms, and the corresponding dispersion value, to obtain a first difference value, further calculates a sum of the smaller one of the representative values and the corresponding dispersion value to obtain a first sum value, and further calculates a difference between the first difference value and the first sum value to obtain the reliability index.

When the reliability index exceeds a threshold, the reliability recognizing section 168 recognizes that the reliability of the TWA feature quantity is high, and, when the reliability index does not exceed the threshold, recognizes that the reliability of the TWA feature quantity is low.

Operation of TWA Measuring Apparatus

Figure 3:
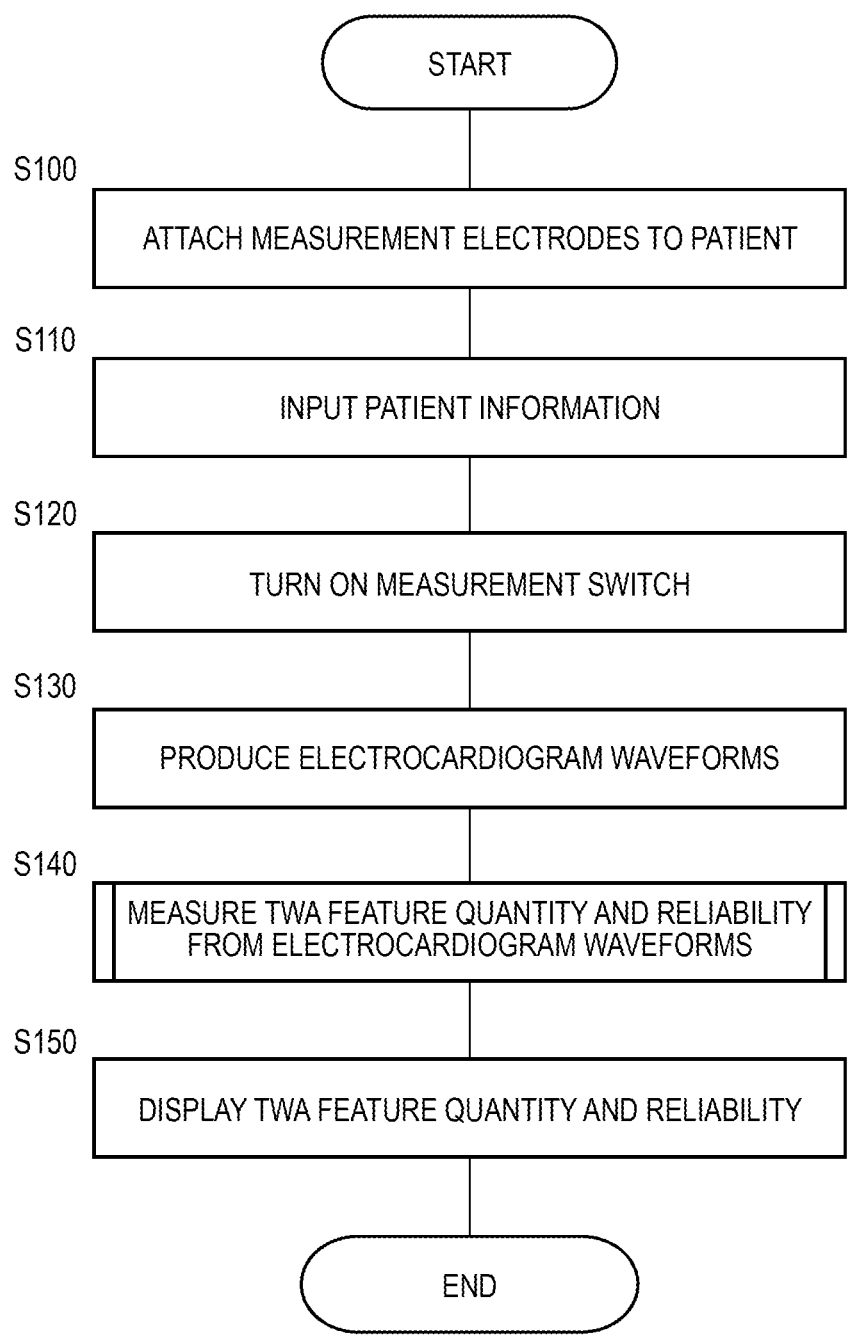
FIG. 3 is an operation flowchart of the TWA measuring apparatuses of FIG. 1.

Next, the operation of the TWA measuring apparatus of Embodiment 1 will be described. FIG. 3 is an operation flowchart of the TWA measuring apparatuses of Embodiment 1.

In the operation flowchart of FIG. 3, the operations of steps S100 to S120 are performed by the operator (measuring person) of the TWA measuring apparatus 100, and the operations of steps S130 and S150 are performed by the electrocardiograph controlling section 110. The operation of step S140 is performed by the electrocardiograph controlling section 110 and the TWA measuring section 160. The operations of steps S100 to S150 correspond also to the procedure of the TWA measuring method of Embodiment 1.

<Step S100>

The operator of the TWA measuring apparatus 100 (electrocardiograph) shown in FIG. 1 attaches the measurement electrodes 120 to predetermined positions of the body surface of the patient. Since the TWA measuring apparatus 100 of Embodiment 1 targets electrocardiograms which are produced by various measuring methods, the measurement electrodes 120 are attached respectively to measurement positions of the patient which are determined in the employed measuring method.

In the case where a derived 12-lead electrocardiogram is to be produced, for example, the measurement electrodes 120 are attached to a total of ten places, i.e., four places or the right and left arms (electrodes L, R) and the right and left lower limbs (electrodes LL, RL) in order to acquire electrocardiographic signals of four limb leads (lead I, lead II, lead III, lead aVR, lead aVL, and lead aVF), and the lower right sternal edge of the fourth intercostal space (lead V1), the lower left sternal edge of the fourth intercostal space (lead V2), the fifth intercostal space in the midclavicular line (lead V4), the midpoint between leads V2 and V4 (lead V3), the left anterior axillary line at the height of V4 (lead V5), and the left middle axillary line at the height of V4 (lead V6) in order to acquire electrocardiographic signals of chest leads (lead V1, lead V2, lead V3, lead V4, lead V5, and lead V6).

<Step S110>

Next, the operator inputs patient information through the patient information inputting section 140. For example, the patient ID, the name of the patient, the age of the patient, and the sex of the patient are input. The input patient information is stored in the patient information storing section 150. The electrocardiogram waveforms which are acquired by the measurement electrodes 120 in the subsequent steps are tagged with the patient information.

<Step S120>

Then, the operator turns ON a measurement switch (not shown) of the TWA measuring electrocardiograph 100. When the measurement switch is turned ON, the measurement of TWA is started.

<Step S130>

The electrocardiograph controlling section 110 produces electrocardiogram waveforms from electrocardiographic signals of the measurement electrodes 120 which are attached in step S100 to the patient. The electrocardiograph controlling section 110 produces the electrocardiogram waveforms by a technique according to the employed measuring method. For example, the electrocardiogram waveforms are produced from the electrocardiographic signals which are acquired by a measuring method such as a Frank's vector electrocardiogram, and a usual scalar electrocardiogram, i.e., a standard 12-lead electrocardiogram, a derived lead electrocardiogram, a Holter electrocardiogram, an event electrocardiogram, an exercise electrocardiogram, and a monitoring electrocardiogram, by the technique according to the measuring method.

<Step S140>

The TWA measuring section 160 measures the TWA feature quantity and the reliability index from the acquired electrocardiogram waveforms. The specific process of the step will be described with reference to the flowchart of FIG. 4.

<Step S150>

The electrocardiograph controlling section 110 causes the displaying section 130 to display the TWA feature quantity and the reliability index which are measured by the TWA measuring section 160.

Figure 4:
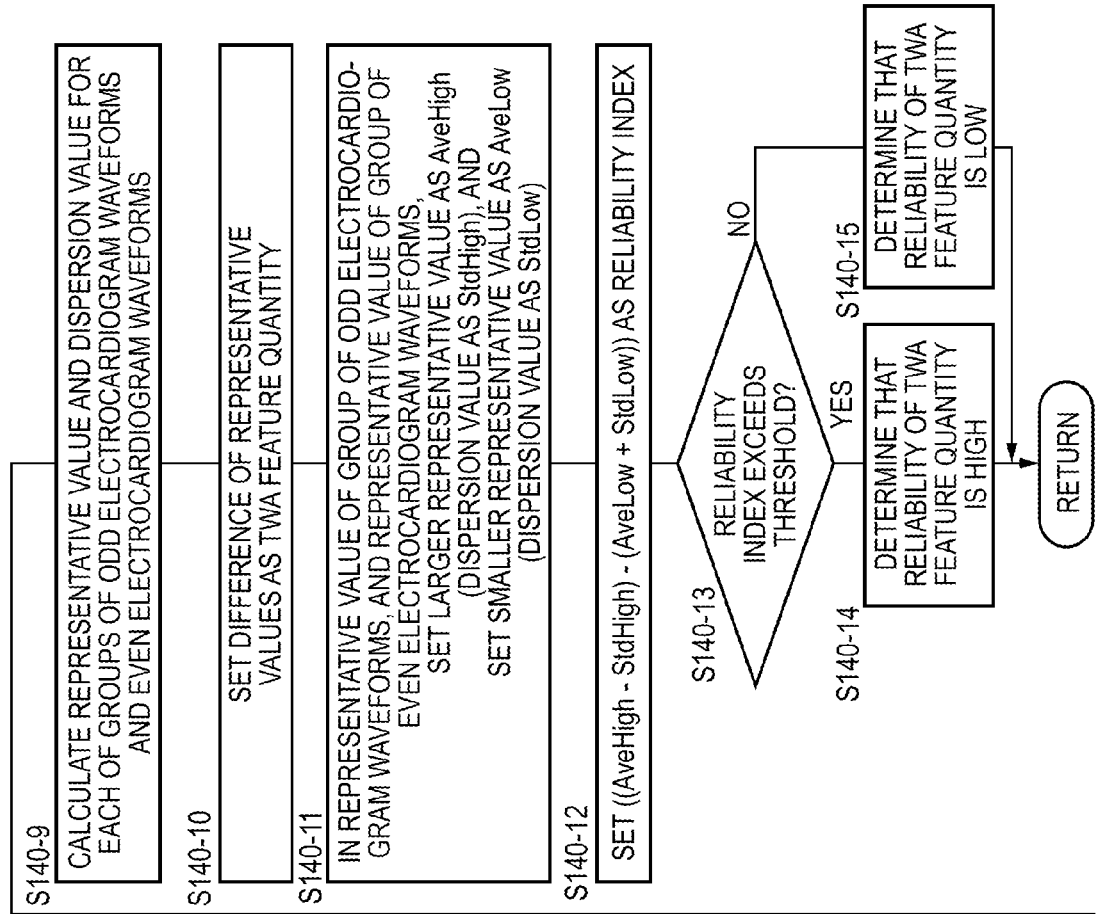
FIG. 4 is a subroutine flowchart of step S140 in the operation flowchart of FIG. 3 (this is applied to Embodiments 1 and 2).
Figure 4:
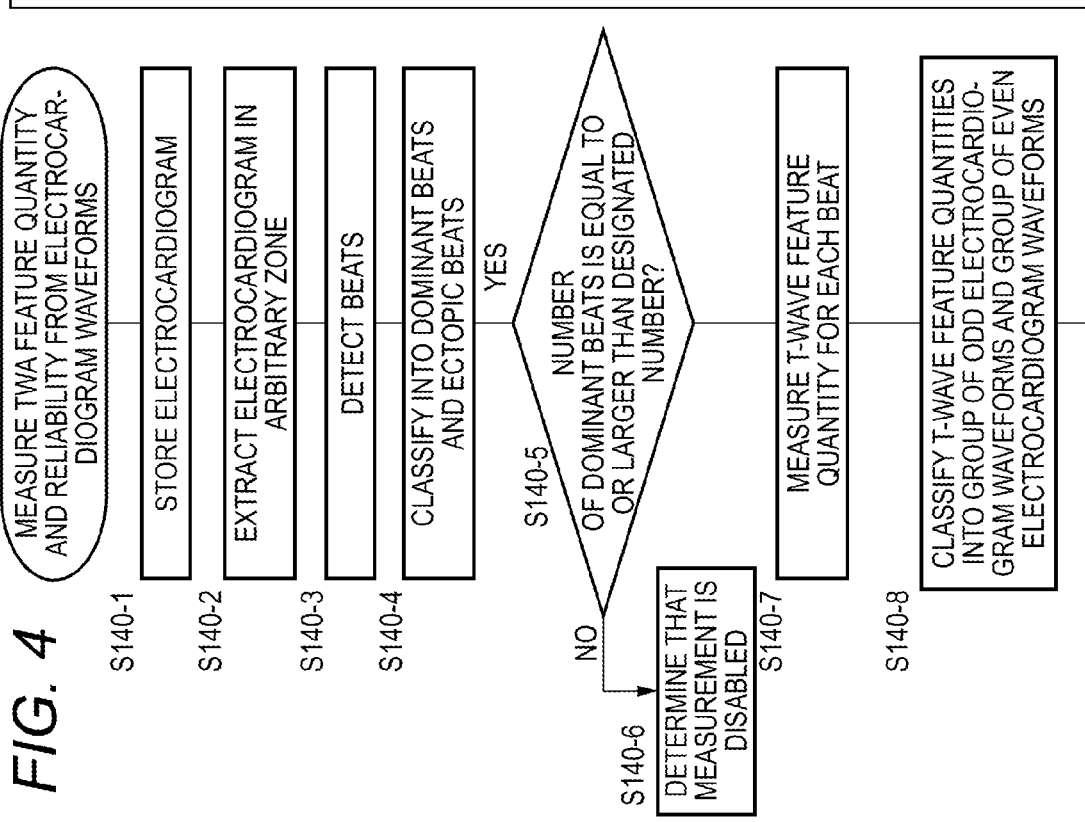

FIG. 4 is a subroutine flowchart of step S140 in the operation flowchart of FIG. 3.

<Step S140-1>

The electrocardiograph controlling section 110 receives the electrocardiogram waveforms acquired by the measurement electrodes 120, and produces an electrocardiogram from the received electrocardiogram waveforms. The produced electrocardiogram is stored in a storage device disposed in the electrocardiograph controlling section 110.

<Step S140-2>

An electrocardiogram in an arbitrary zone (time zone), for example, 20 seconds is extracted from the electrocardiogram stored in the storage device.

<Steps S140-3 and S140-4>

The electrocardiograph controlling section 110 detects beats from the extracted electrocardiogram, and classifies all the detected beats into a dominant beat and an ectopic beat. This classification is performed in the following manner. The patterns of all beats are classified. Beats of the most pattern are set as the dominant beats, and all the other beats are set as the ectopic beats.

<Step S140-5>

The electrocardiograph controlling section 110 determines whether there is no classified ectopic beat or not, and whether the number of the dominant beats is equal to or larger than a designated number or not. For example, the electrocardiograph controlling section 110 determines whether the number of the dominant beats is equal to or larger than 10 or not. This is because, when the number of the classified dominant beats is smaller than a certain value, the reliability as the TWA feature quantity and reliability index which will be described later cannot be ensured.

<Step S140-5: NO, S140-6>

If the number of the classified dominant beats is not equal to or larger than the designated value, the reliabilities of the TWA feature quantity and the reliability index cannot be ensured, and the electrocardiograph controlling section 110 therefore determines that the measurement is disabled, and causes the displaying section 130 to display the determination.

<Step S140-5: YES, S140-7>

Figure 5:
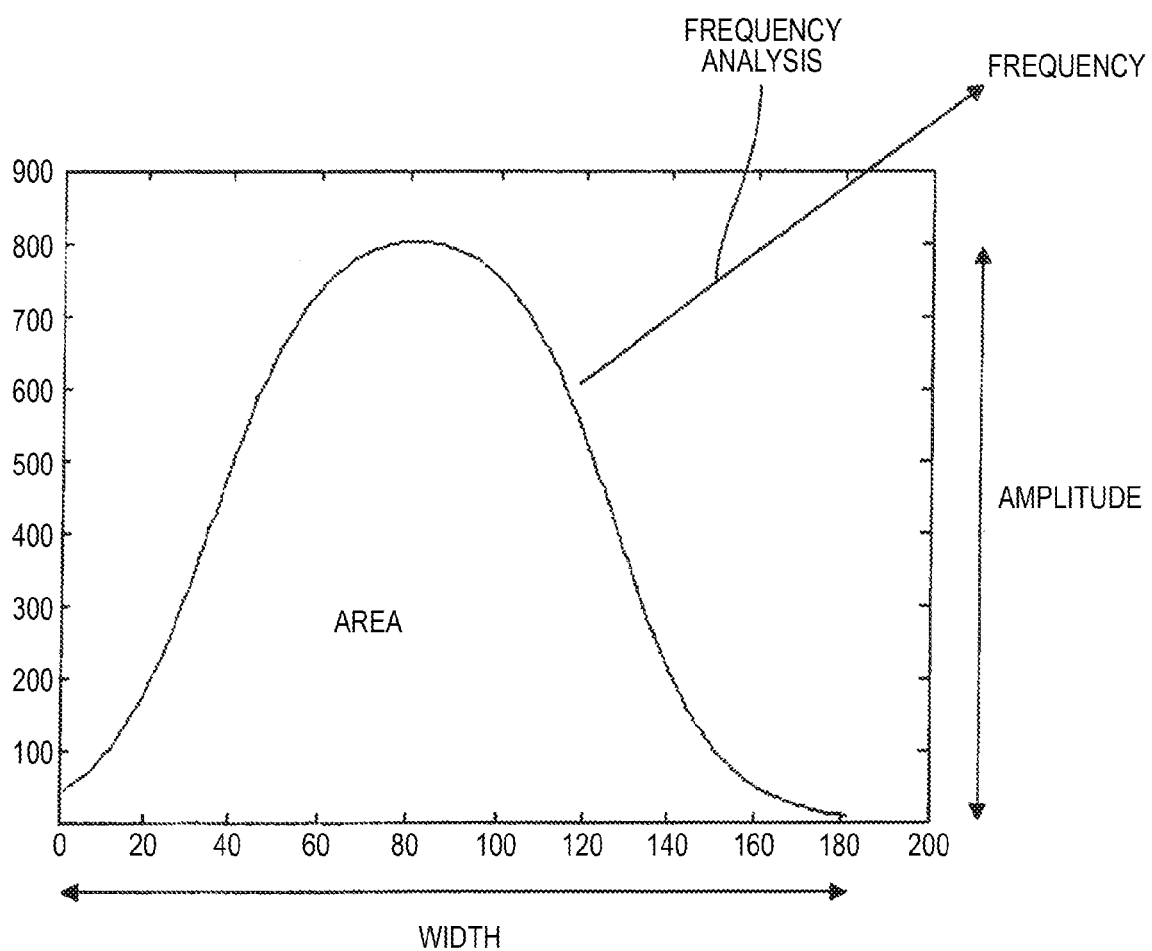
FIG. 5 is a view illustrating kinds of TWA feature quantities (this is applied to Embodiments 1 and 2).

If the number of the classified dominant beats is equal to or larger than the designated value, the T-wave feature quantity measuring section 162 receives the dominant beats extracted by the electrocardiograph controlling section 110, and measures the T-wave feature quantity for each of the beats. As shown in FIG. 5, the T-wave feature quantity is one of the width, amplitude, and area of a T-wave contained in the beat, and the frequency that is obtained by a frequency analysis, or a value which is obtained by performing a four arithmetic operation on an arbitrary combination of these values. Examples of the four arithmetic operation are (width×amplitude), and (amplitude÷width). As a result of the process of this step, the T-wave feature quantity of each beat is measured.

<Step S140-8>

The classifying section 164 classifies the T-wave feature quantities of the electrocardiogram waveforms which are measured by the T-wave feature quantity measuring section 162, into the group of odd electrocardiogram waveforms and the group of even electrocardiogram waveforms because, in TWA, the T waves of odd and even beats are alternately changed as described above.

<Step S140-9>

The reliability index calculating section 166 calculates the representative value and dispersion value of the T-wave feature quantities of the electrocardiogram waveforms which are classified into the group of odd electrocardiogram waveforms by the classifying section 164. Further, the reliability index calculating section 166 calculates the representative value and dispersion value of the T-wave feature quantities of the electrocardiogram waveforms which are classified into the group of even electrocardiogram waveforms by the classifying section 164. Namely, the representative value and dispersion value of the T-wave feature quantities are calculated for each group. Here, the representative value and dispersion value of the T-wave feature quantities are values which are obtained by statistically processing the T-wave feature quantities. For example, the representative value is the average or medium of the T-wave feature quantities, and the dispersion value is the standard deviation or root mean square of the T-wave feature quantities. In the embodiment, the average of the T-wave feature quantities is employed as the representative value of the T-wave feature quantities, and the standard deviation of the T-wave feature quantities is employed as the dispersion value of the T-wave feature quantities.

<Step S140-10>

The reliability index calculating section 166 obtains the difference between the representative values of the T-wave feature quantities of the groups, and sets the difference as the TWA feature quantity. In the embodiment, the average of the amplitudes of T waves is employed as the representative value of the T-wave feature quantities.

In this case, when the amplitudes of an N number of T waves in the group of odd electrocardiogram waveforms are $Ln1, Ln2, Ln3, \ldots, LnN$, for example, the representative value A of the T-wave feature quantities can be obtained by $(Ln1+Ln2+Ln3+\ldots+LnN)/N$. When the amplitudes of an M number of T waves in the group of even electrocardiogram waveforms are $Lm1, Lm2, Lm3, \ldots, LmM$, the representative value B of the T-wave feature quantities can be obtained by $(Lm1+Lm2+Lm3+\ldots+LmM)/M$.

Therefore, the TWA feature quantity is the absolute value of a difference of the representative value A and the representative value B. When the thus obtained TWA feature quantities are plotted, they are distributed as indicated by filled circles and open circles in FIGS. 6A and 7A.

<Step S140-11>

Next, the reliability index calculating section 166 sets the larger T-wave feature quantity in the representative values of the T-wave feature quantities in the groups of odd and even electrocardiogram waveforms, as AveHigh, and the corresponding dispersion value as StdHigh. Similarly, the reliability index calculating section 166 sets the smaller T-wave feature quantity as AveLow, and the corresponding dispersion value as StdLow.

<Step S140-12>

The reliability index calculating section 166 calculates an expression (AveHigh−StdHigh)−(AveLow+StdLow). Namely, the reliability index calculating section 166 calculates the difference (first difference value) between the representative value and the dispersion value of the group in which the T-wave feature quantities are large, and the sum (first sum value) of the representative value and the dispersion value of the group in which the T-wave feature quantities are small, and further calculates the difference between the first difference value and the first sum value.

The value (AveHigh−StdHigh), namely the first difference value indicates (the representative value (average)−the dispersion value) of the group in which the T-wave feature quantities are large, and is expressed by the filled circle at the lower end of each line segment in which the both ends are indicated by the filled circles in FIG. 6B. The value (AveLow+StdLow), namely the first sum value indicates (the representative value (average)+the dispersion value) of the group in which the T-wave feature quantities are small, and is expressed by a cross at the upper end of each line segment in which the both ends are indicated by crosses in FIG. 6B.

Figure 7A:
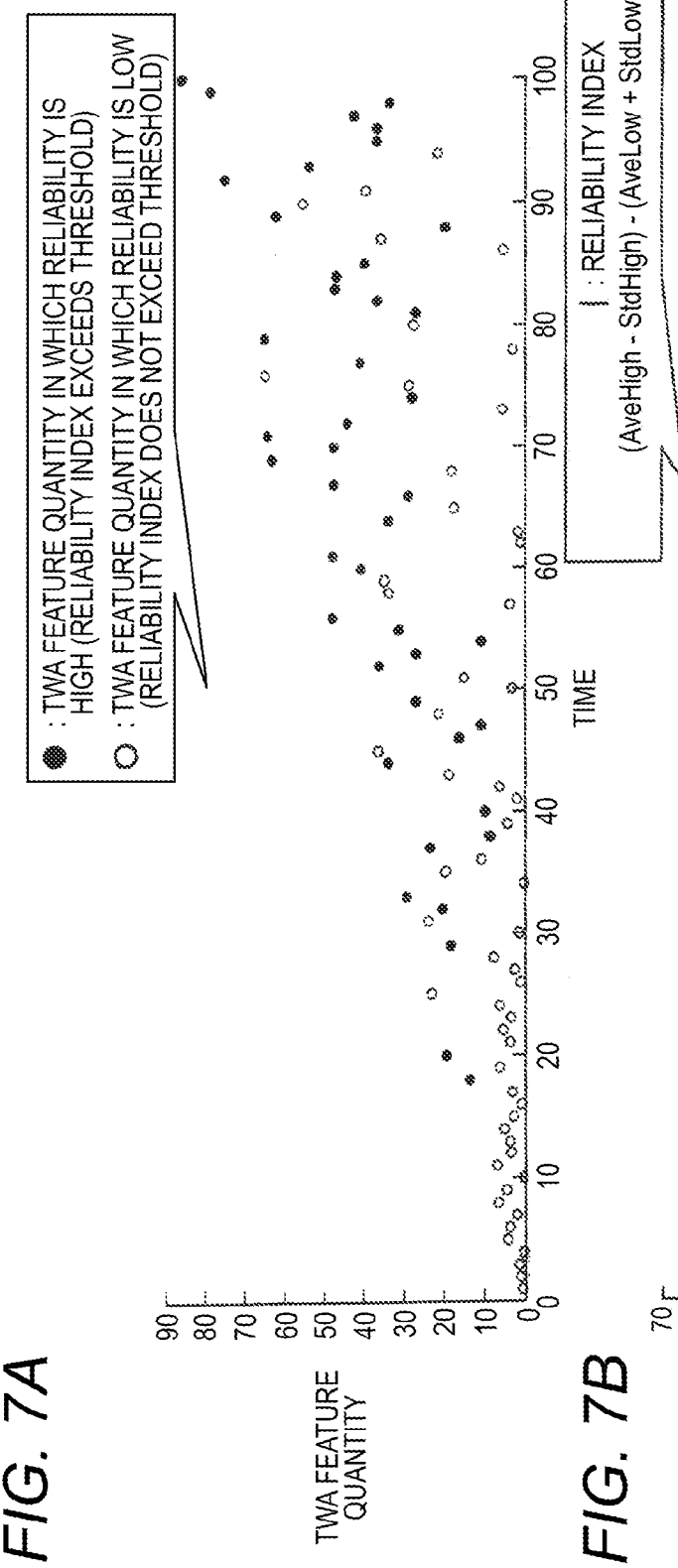
FIG. 7A is a view illustrating the TWA feature quantities.
Figure 7B:
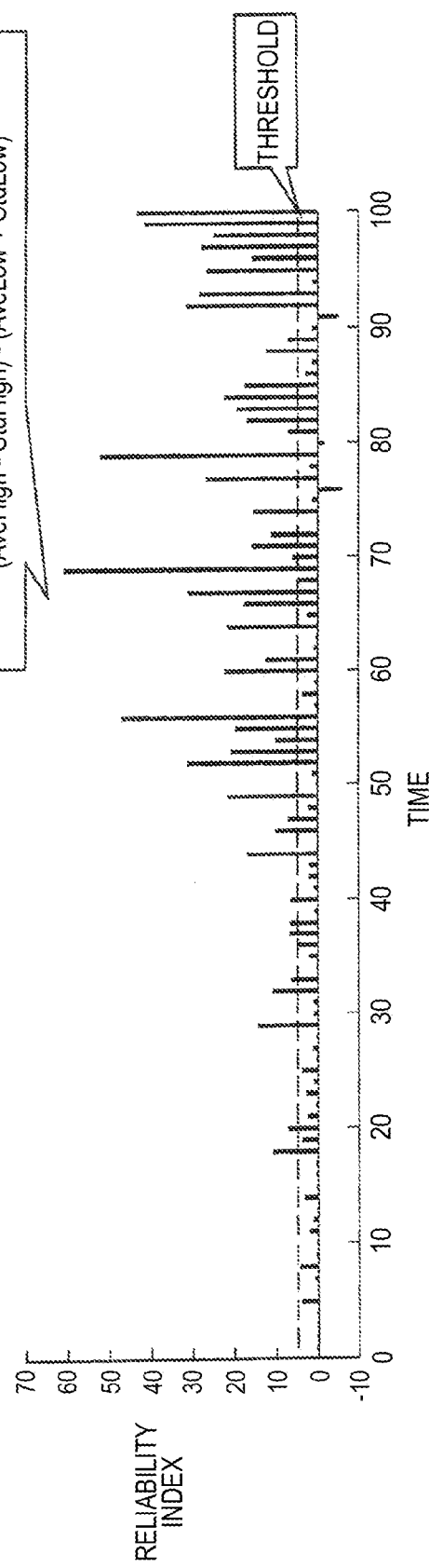
FIG. 7B is a view illustrating a reliability indexes (applied to Embodiments 1 and 2).

When the expression (AveHigh−StdHigh)−(AveLow+StdLow) is calculated, the bar graph such as shown in FIG. 7B is produced.

<Step S140-13>

The reliability recognizing section 168 determines whether the reliability indexes calculated by the reliability index calculating section 166 exceed the threshold or not. The threshold is stored in the reliability recognizing section 168.

<Step S140-13: YES, S140-14>

In the bar graph shown in FIG. 7B, the threshold for determining the level of the reliability of the TWA feature quantity is drawn. If the reliability index calculated by the reliability index calculating section 166 exceeds the threshold, the reliability recognizing section 168 determines that the reliability of the TWA feature quantity is high.

<Step S140-13: NO, S140-15>

By contrast, if the reliability index calculated by the reliability index calculating section 166 does not exceed the threshold, the reliability recognizing section 168 determines that the reliability of the TWA feature quantity is low.

When the processes of steps S140-13, S140-14, and S140-15 are performed, the reliability of the TWA feature quantity is indicated by the filled circles and the open circles in FIGS. 6A and 7A. The filled circle indicates the TWA feature quantity in which the reliability index exceeds the threshold, and shows that the reliability is high. On the other hand, the open circle indicates the TWA feature quantity in which the reliability index does not exceed the threshold, and shows that the reliability is low. The measured TWA feature quantities and reliability indexes are displayed on the displaying section 130 to assist the operator to determine whether TWA exists or not.

In the case where the reliability of the TWA feature quantity is considered as described above, even when the measured TWA feature quantity is 48 μV, for example, it is determined that the reliability is high. By contrast, in the case where, even when the measured TWA feature quantity is 50 μV, it is determined that the reliability is low, it is possible to obtain the conviction that the measured value of 48 μV is very correct, but it is possible to obtain the conviction that the measured value of 50 μV is not very reliable. When referring to the reliability index, therefore, the operator can accurately determine whether TWA exists or not.

Embodiment 2

Next, a TWA measuring apparatus and TWA measuring method of Embodiment 2 will be described. In the embodiment, the states of odd and even beats, and the reliability of the TWA feature quantity are known from electrocardiogram waveforms of odd and even beats which are acquired from the outside by an electrocardiogram data inputting section. The TWA measuring apparatus and TWA measuring method of the embodiment are different from those of Embodiment 1 only in that electrocardiogram waveforms are not obtained from the measurement electrodes.

Configuration of TWA Measuring Apparatus

Figure 8:
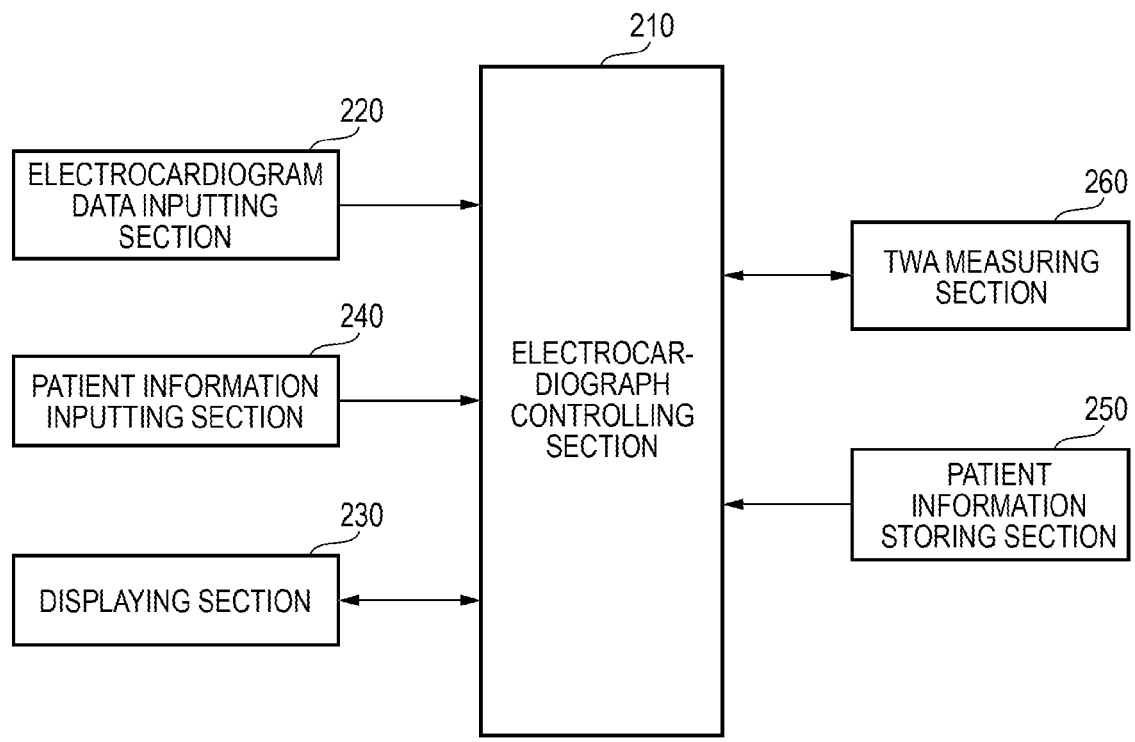
FIG. 8 is a block diagram of a TWA measuring apparatus of Embodiment 2.

FIG. 8 is a block diagram of the TWA measuring apparatus of Embodiment 2. Also the TWA measuring apparatus of Embodiment 2 is disposed in an electrocardiograph.

As shown in the figure, the TWA measuring apparatus 200 includes an electrocardiograph controlling section 210, an electrocardiogram data inputting section 220, a displaying section 230, a patient information inputting section 240, a patient information storing section 250, and a TWA measuring section 260.

The electrocardiograph controlling section 210 generally controls the operations of the electrocardiogram data inputting section 220, the displaying section 230, the patient information inputting section 240, the patient information storing section 250, and the TWA measuring section 260.

The electrocardiogram data inputting section 220 is a data reading device or data inputting device which is configured so as to be accessible to a recording medium such as a CD-ROM or a HD, or an information processing apparatus such as PC, the medium or the apparatus storing electrocardiogram data. The electrocardiogram data include an electrocardiographic signal acquired by a measuring method such as a Frank's vector electrocardiogram, and a usual scalar electrocardiogram, i.e., a standard 12-lead electrocardiogram, a derived lead electrocardiogram, a Holter electrocardiogram, an event electrocardiogram, an exercise electrocardiogram, and a monitoring electrocardiogram.

The displaying section 230, the patient information inputting section 240, the patient information storing section 250, and the TWA measuring section 260 are identical with the displaying section 130, patient information inputting section 140, patient information storing section 150, and TWA measuring section 160 which have been described in Embodiment 1, respectively. The functions of these components have been described in Embodiment 1.

Operation of TWA Measuring Apparatus

Figure 9:
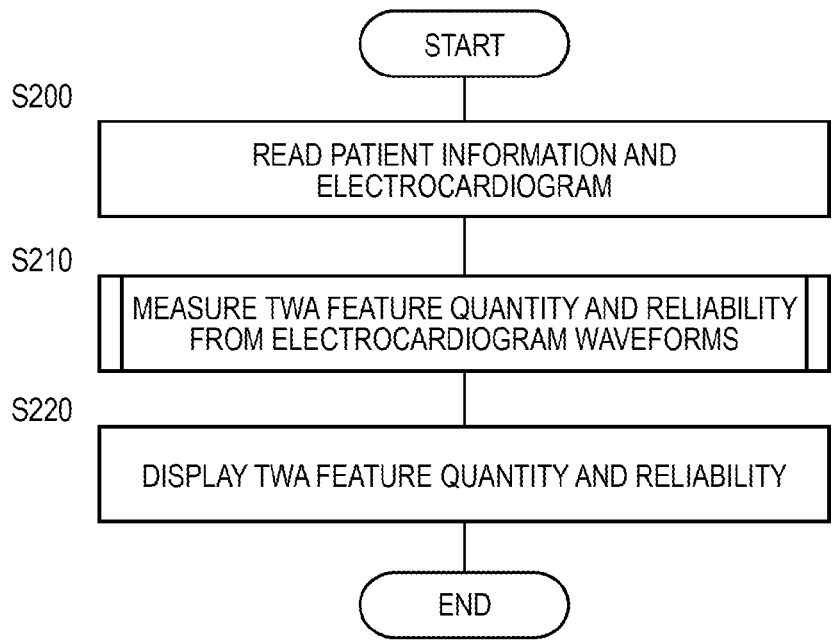
FIG. 9 is an operation flowchart of the TWA measuring apparatuses of FIG. 8.

Next, the operation of the TWA measuring apparatus of Embodiment 2 will be described. FIG. 9 is an operation flowchart of the TWA measuring apparatuses of Embodiment 2.

In the operation flowchart of FIG. 9, the operation of step S200 is performed by the electrocardiograph controlling section 210, and the operations of steps S210 and S220 are performed by the electrocardiograph controlling section 210 and the TWA measuring section 260.

<Step S200>

The operator of the TWA measuring apparatus 200 (electrocardiograph) shown in FIG. 8 accesses a recording medium such as a CD-ROM or a HD, or an information processing apparatus such as PC, the medium or the apparatus storing electrocardiograms of patients, and reads patient information and an electrocardiogram of the patient. The patient information and electrocardiogram of the patient which are read are stored in a storage device disposed in the electrocardiograph controlling section 210.

<Step S210>

The TWA measuring section 260 measures the TWA feature quantity and the reliability index from the stored electrocardiogram. The specific process of the step is identical with the process of the flowchart of FIG. 4 which has been described in Embodiment 1.

<Step S220>

The electrocardiograph controlling section 210 causes the displaying section 230 to display the TWA feature quantity and reliability index which are measured in step S210 by the TWA measuring section 260.

As described above, according to the TWA measuring apparatus and TWA measuring method of the presently disclosed subject matter, the T-wave feature quantity is measured for each beat, the measured T-wave feature quantities are classified into the group of odd electrocardiogram waveforms and that of even electrocardiogram waveforms, and the representative value and dispersion value of the T-wave feature quantities in each group are calculated. Therefore, the states of odd and even beats can be known. The knowing of the states of odd and even beats is effective in ensuring the reliability of the TWA feature quantity.

According to an aspect of the presently disclosed subject matter, the T-wave feature quantity is measured for each beat, the measured quantities are classified into the group of odd electrocardiogram waveforms and that of even electrocardiogram waveforms, and the representative value and dispersion value of the T-wave feature quantities in each of the groups are calculated. Therefore, the states of odd and even beats can be known. Since the states of odd and even beats are known, moreover, the reliability of the TWA feature quantity can be ensured.

What is claimed is:

1. A T-wave alternans (TWA) measuring apparatus comprising:
    a T-wave feature quantity measuring section which is configured to measure T-wave feature quantities of electrocardiogram waveforms acquired from a subject;
    a classifying section which is configured to classify the T-wave feature quantities into a group of odd electrocardiogram waveforms and a group of even electrocardiogram waveforms;
    a reliability index calculating section which is configured to calculate:
        a first representative value and a first dispersion value of the T-wave feature quantities in the group of odd electrocardiogram waveforms, and a second representative value and a second dispersion value of the T-wave feature quantities in the group of even electrocardiogram waveforms;
        a difference between the first and second representative values, to obtain a TWA feature quantity; and
        an adjustment value between the first representative value and the first dispersion value, and an adjustment value between the second representative value and the second dispersion value, to obtain a reliability index;
    a reliability recognizing section which is configured to recognize:
        when the reliability index exceeds a threshold, that reliability of the TWA feature quantity is high; and
        when the reliability index does not exceed the threshold, that the reliability of the TWA feature quantity is low; and
    an output section configured to output the TWA feature quantity and the reliability index, wherein the reliability index calculating section calculates:
        when the first representative value is larger than the second representative value, a difference between the first representative value and the first dispersion value, to obtain a first difference value, and a sum of the second representative value and the second dispersion value, to obtain a first sum value; and,
        when the first representative value is smaller than the second representative value, a difference between the second representative value and the second dispersion value, to obtain a first difference value, and a sum of the first representative value and the first dispersion value, to obtain a first sum value, and
    wherein the reliability index calculating section calculates a difference between the first difference value and the first sum value, to obtain the reliability index,
    wherein the T-wave quantity measuring section, the classifying section, the reliability index section, and the reliability recognizing section, are executed by a processor.

2. The TWA measuring apparatus according to claim 1, wherein the output section is a display configured to display the TWA feature quantity and the reliability index.

3. The TWA measuring device of claim 1, wherein the TWA measuring device is part of an electrocardiograph.

4. A T-wave alternans (TWA) measuring method comprising:
    measuring T-wave feature quantities of electrocardiogram waveforms acquired from a subject;
    classifying the T-wave feature quantities into a group of odd electrocardiogram waveforms and a group of even electrocardiogram waveforms;
    calculating:
        a first representative value and a first dispersion value of the T-wave feature quantities in the group of odd electrocardiogram waveforms, and a second representative value and a second dispersion value of the T-wave feature quantities in the group of even electrocardiogram waveforms;
        a difference between the first and second representative values, to obtain a TWA feature quantity; and
        an adjustment value between the first representative value and the first dispersion value, and an adjustment value between the second representative value and the second dispersion value, to obtain a reliability index; and
    recognizing:
        when the reliability index exceeds a threshold, that the reliability of the TWA feature quantity is high; and,
        when the reliability index does not exceed the threshold, that the reliability of the TWA feature quantity is low;
    outputting the TWA feature quantity and the reliability index,
    wherein, in the calculating process,
    when the first representative value is larger than the second representative value, a difference between the first representative value and the first dispersion value is calculated, to obtain a first difference value, and a sum of the second representative value and the second dispersion value is calculated, to obtain a first sum value; and
    when the first representative value is smaller than the second representative value, a difference between the second representative value and the second dispersion value is calculated, to obtain a first difference value, and a sum of the first representative value and the first dispersion value is calculated, to obtain a first sum value, and wherein a difference between the first difference value and the first sum value is calculated, to obtain the reliability index.

5. The TWA measuring method according to claim 4, wherein the outputting comprises:
displaying the TWA feature quantity and the reliability index.

6. The TWA measuring method according to claim 4, wherein,
the measuring process comprises:
storing the electrocardiogram waveforms acquired from the subject; and
measuring the T-wave feature quantities of the stored electrocardiogram waveforms.

7. The TWA measuring method according to claim 6, wherein
the process of measuring the T-wave feature quantities of the stored electrocardiogram waveforms comprises:
determining whether, with respect to the stored electrocardiogram waveforms, a beat is a dominant beat or an ectopic beat; and,
when a number of the dominant beats is not equal to or larger than a designated number, determining that the measurement is disabled, and,
when the number of the dominant beats is equal to or larger than the designated number, extracting an electrocardiograph of a zone where only the dominant beats exist.

8. The TWA measuring method according to claim 4, wherein
the first and second representative values and the first and second dispersion values of the T-wave feature quantities are values which are obtained by statistically processing the T-wave feature quantities.

9. The TWA measuring method according to claim 8, wherein
each of the first and second representative values of the T-wave feature quantities is an average or medium of the T-wave feature quantities, and
each of the first and second dispersion values of the T-wave feature quantities is a standard deviation or root mean square of the T-wave feature quantities.

10. The TWA measuring method according to claim 4, wherein
each of the T-wave feature quantities is one of a width, amplitude, area, and frequency of a T-wave of the corresponding one of the electrocardiogram waveforms, or a value which is obtained by performing a four arithmetic operation on an arbitrary combination of the width, amplitude, area, and frequency.

11. The TWA measuring method according to claim 4, further comprising:
obtaining electrocardiographic signals via a plurality of electrodes attached to a body of a patient; and
obtaining the electrocardiogram waveforms from the obtained electrocardiographic signals,
wherein the measuring of the T-wave feature quantities comprises measuring the T-wave feature quantities of the obtained electrocardiogram waveforms.

12. The TWA measuring method according to claim 4, wherein the measuring, the classifying, the calculating, and the recognizing, are executed by an electrocardiograph.

13. An electrocardiograph comprising:
an electrode measurement section comprising a plurality of electrodes to be attached to a body surface of a patient, and is configured to obtain electrocardiographic signals;
a T-wave alternans (TWA) measuring apparatus; and
a controller configured to control the electrode measurement section and the TWA measuring apparatus and is configured to produce electrodiogram waveforms from the electrocardiographic signals obtained by the electrode measurement section;
wherein the TWA measuring apparatus comprises:
a T-wave feature quantity measuring section which is configured to measure T-wave feature quantities of electrocardiogram waveforms based on the electrocardiogram waveforms produced by the controller;
a classifying section which is configured to classify the T-wave feature quantities into a group of odd electrocardiogram waveforms and a group of even electrocardiogram waveforms;
a reliability index calculating section which is configured to calculate:
a first representative value and a first dispersion value of the T-wave feature quantities in the group of odd electrocardiogram waveforms, and a second representative value and a second dispersion value of the T-wave feature quantities in the group of even electrocardiogram waveforms;
a difference between the first and second representative values, to obtain a TWA feature quantity; and
an adjustment value between the first representative value and the first dispersion value, and an adjustment value between the second representative value and the second dispersion value, to obtain a reliability index; and
a reliability recognizing section which is configured to recognize:
when the reliability index exceeds a threshold, that reliability of the TWA feature quantity is high; and
when the reliability index does not exceed the threshold, that the reliability of the TWA feature quantity is low,
wherein the reliability index calculating section calculates:
when the first representative value is larger than the second representative value, a difference between the first representative value and the first dispersion value, to obtain a first difference value, and a sum of the second representative value and the second dispersion value, to obtain a first sum value; and,
when the first representative value is smaller than the second representative value, a difference between the second representative value and the second dispersion value, to obtain a first difference value, and a sum of the first representative value and the first dispersion value, to obtain a first sum value, and
wherein the reliability index calculating section calculates a difference between the first difference value and the first sum value, to obtain the reliability index.

* * * * *